(12) United States Patent
Shiba

(10) Patent No.: US 7,060,203 B2
(45) Date of Patent: Jun. 13, 2006

(54) ELECTROLYTE SOLUTION FOR PARTICLE MEASURING APPARATUS, AND PARTICLE MEASURING METHOD USING SAME

(75) Inventor: Kouhei Shiba, Ono (JP)

(73) Assignee: Sysmex Corporation, Hyogo (JP)

( * ) Notice: Subject to any disclaimer, the term of this patent is extended or adjusted under 35 U.S.C. 154(b) by 446 days.

(21) Appl. No.: 09/984,565

(22) Filed: Oct. 30, 2001

(65) Prior Publication Data

US 2002/0079225 A1    Jun. 27, 2002

(30) Foreign Application Priority Data

Oct. 30, 2000  (JP) ............... 2000-330893
Sep. 14, 2001  (JP) ............... 2001-280571

(51) Int. Cl.
*C25D 5/00*  (2006.01)
*C25D 21/12* (2006.01)
*G01N 15/00* (2006.01)

(52) U.S. Cl. .............. 252/408.1; 252/500; 252/518.1; 252/519.3; 73/865.5; 436/10; 205/81

(58) Field of Classification Search ............ 252/408.1, 252/500, 518.1, 519.3; 73/865.5; 436/10, 436/43; 250/573; 356/73, 39; 514/222; 205/81

See application file for complete search history.

(56) References Cited

U.S. PATENT DOCUMENTS

| | | | |
|---|---|---|---|
| 3,444,463 A | 5/1969 | Coulter et al. | |
| 3,444,464 A | 5/1969 | Coulter et al. | |
| 3,514,581 A * | 5/1970 | Rocholl et al. | ............. 219/522 |
| 4,346,018 A | 8/1982 | Carter et al. | |
| 4,506,018 A | 3/1985 | North, Jr. | |
| 4,659,497 A | 4/1987 | Akred et al. | |
| 5,274,431 A | 12/1993 | Kuroda | |
| 5,325,168 A | 6/1994 | Nakamoto et al. | |
| 5,325,169 A | 6/1994 | Nakamoto et al. | |
| 5,631,165 A | 5/1997 | Chupp et al. | |
| 5,656,499 A | 8/1997 | Chupp et al. | |
| 5,721,433 A | 2/1998 | Kosaka | |
| 6,037,116 A * | 3/2000 | Wiggins et al. | ............... 435/1.1 |
| 2003/0110871 A1 * | 6/2003 | Malachowski et al. | .. 73/864.81 |

FOREIGN PATENT DOCUMENTS

| | | |
|---|---|---|
| JP | SHO 52-58993 | 5/1977 |
| JP | HEI 1-33780 | 7/1989 |
| JP | 03-015757 | 1/1991 |
| JP | HEI 3-27865 | 4/1991 |
| JP | 06-016538 * | 1/1994 |
| JP | HEI 10-160730 | 6/1998 |

OTHER PUBLICATIONS

"Measurements, Techniques of Particle Diameter" (edited by The Society of Powder Technology, JAPAN) Oct. 29, 1999, Japan & English Translation.

Zhi Wang et al., "Separation of lidocane and its metabolites by capillary electrophoresis using volatile aqueous and nonaqueous electrolyte systems," Electrophoresis 2001; 22, 2495-2502.

* cited by examiner

*Primary Examiner*—Mark Kopec
*Assistant Examiner*—Kallambella Vijayakumar
(74) *Attorney, Agent, or Firm*—Hunton & Williams

(57) ABSTRACT

An electrolyte solution for a particle measuring apparatus which comprises an inorganic salt, such as sodium chloride or calcium chloride, dissolved in an organic solvent. A substance that promotes dissolution of inorganic salts is added to provide the organic solvent with sufficient electric conductivity for electrical particle measurement. Such substances include either or both: Compound (a): a zwitterionic compound or compounds, and Compound (b): a compound or compounds including a hydroxyl group and a carboxyl or an amino group in the same molecule.

10 Claims, 3 Drawing Sheets

ELECTROLYTE SOLUTION FOR PARTICLE MEASURING APPARATUS, AND PARTICLE MEASURING METHOD USING SAME

CROSS-REFERENCE TO RELATED APPLICATION

This application relates to Japanese Patent Application No.2000-330893 filed on Oct. 30, 2000, and Japanese Patent Application No.2001-280571 filed on Sep. 14, 2001, priorities to both of which are claimed under 35 USC § 119, and disclosures of both of which are incorporated herein by reference in their entirety.

BACKGROUND OF THE INVENTION

1. Field of the Invention

The present invention relates to an electrolyte solution used in an electrical or optical particle measuring apparatus. More specifically, it relates to an electrolyte solution comprising an organic solvent as the solvent.

2. Related Art

It is common to conduct measurement of the numbers and sizes of different types of particles of cells in blood or urine samples or of fine ceramics, pigments, toners and the like. Such particle measurement has been achieved based on optical or electric measuring principles.

One example of an optical method is the method in which: a sample containing the particles to be measured is continuously fed through a flow cell, the flow cell is irradiated with laser light, and optical information such as scattered light or fluorescent light is obtained to detect the presence of the particles or the sizes of the particles. Another example entails imaging particles in a flow cell with a video camera and analyzing the image.

Various optical measuring apparatuses for automatic measurement of particles by such optical methods are proposed in U.S. Pat. No. 5,325,168, U.S. Pat. No. 5,325,169 and U.S. Pat. No. 5,721,433, and elsewhere.

On the other hand, electrical particle measuring methods generate information about particles by means of an orifice between electrodes through which a current flows. A sample solution containing the particles is passed through the orifice and the change in impedance between the electrodes is detected as the particles pass through the orifice. In one such electrical method, the particles are passed through an orifice in which a direct current flows, and the change in impedance is obtained as a pulse signal. The degree of change in the pulse signal differs depending on the sizes (volumes) of the particles.

In another electrical method, the particles are passed through the orifice through which a high frequency current flows, and the change in impedance is obtained as a pulse signal. When high density portion sand low density portions are present in a single particle, the impedance of each for the high frequency current will differ, and therefore internal information on the particles can be obtained. For example, it is possible to obtain information on the sizes and density of the nuclei in cells such as leukocytes.

Various apparatuses for automatic measurement of particles by such electrical methods are proposed in U.S. Pat. No. 3,444,463, U.S. Pat. No. 3,444,464, U.S. Pat. No. 5,274,431, and elsewhere. These apparatuses, however, often exhibit problems including: the detection signal differs depending on the position at which the particles pass through the orifice, multiple particles sometimes pass through the orifice in close proximity and are measured as a single particle, or particles that have passed through the pore accumulate around the orifice and flow backward, creating noise. In order to solve these problems, a sheath flow system is often used in combination therewith.

In a sheath flow system, the sample solution containing the particles is surrounded by a sheath solution before passing through the orifice. This solves the aforementioned problem because the sample solution is hydrodynamically constricted at the center of the sheath solution flowing, in a laminar flow state ("sheath flow"), and the particles therefore pass through the orifice in a highly precise single file. Sheath flow systems are also widely used for optical particle measuring apparatuses. They allow continuous feeding of particles in a precise manner in a limited detection zone.

In an electrical particle measuring apparatus, the orifice and electrodes must be filled with the electrolyte solution at the time of measurement. That is, the sample solution, i.e., the dispersion medium for dispersion of the particles (hereafter "dispersion medium"), and the sheath solution must be electrolyte solutions.

The solvent used for the electrolyte solution is most commonly water. This is because dissolution of a salt such as sodium chloride in the water provides electrolyte solutions with the electric conductivity required for particle measurement. Since the measurement is preferably carried out without affecting the sizes or shapes of the particles, a saline solution containing a buffer or preservative is usually used for measurement of cells such as blood cells. For example, Japanese Unexamined Patent Publication SHO No. 52-58993, Japanese Examined Patent Publication HEI No. 1-33780 and Japanese Examined Patent Publication HEI No.3-27865 disclose diluents for electrical particle measuring apparatuses using water as the solvent. Japanese Unexamined Patent Publication HEI No. 10-160730 discloses the use of buffered saline in an impedance transducer cell analyzer for count and size sorting of erythrocytes and platelets.

However, when the objects of measurement are water-soluble particles such as ingestible drugs or foods, detergent granules, or certain pigments, water cannot be used as the solvent for the electrolyte solution. That is because the particles dissolve, making it difficult to accurately measure the numbers and sizes of the particles.

Moreover, depending on the type of particles to be measured, using water as the solvent for the electrolyte solution can cause aggregation. Therefore, water is not preferred as the solvent of the electrolyte solution for certain types of particles. Aggregation of the particles makes it difficult to accurately measure the numbers and sizes of the particles.

In such cases, therefore, particle measurement requires an organic solvent as the electrolyte solution solvent, instead of water. But since organic solvents exhibit almost no electric conductivity, the use of an organic solvent requires dissolution of some type of salt in the solution to provide the conductivity necessary for particle measurement.

The types of salts that dissolve in organic solvents are limited. However, it is known that the inorganic salts lithium chloride and lithium perchlorate dissolve in organic solvents. Accordingly, solutions of lithium perchlorate in organic solvents such as methanol or isopropanol have been used as electrolyte solutions to increase electric conductivity in electrical particle measuring apparatuses.

However, lithium chloride and lithium perchlorate accelerate corrosion of the apparatuses. This suggests using inorganic salts other than lithium chloride and lithium perchlorate, for example, sodium chloride or calcium chloride. However, inorganic salts such as sodium chloride are less soluble in organic solvents than in water, and it has therefore been difficult to increase conductivity enough to allow particle measurement.

Organic salts such as sodium acetate or sodium citrate are also known to dissolve satisfactorily in organic solvents such as methanol and thereby increase conductivity. However, organic salts tend to cause the particles to aggregate, which hinders measurement of the particle size distribution.

On the other hand, organic solvents have conventionally been used in dispersion media or sheath solutions for optical particle measurement. Unlike with electrical particle measurement, there is no need to increase the conductivity of the organic solvent. However, when the dispersion medium or sheath solution contains such an organic solvent, it can only be used for optical particle measurement and not for electrical particle measurement.

SUMMARY OF THE INVENTION

The present invention provides an electrolyte solution for a particle measuring apparatus which employs an organic solvent with sufficient electrical conductivity.

According to the invention, a substance that promotes dissolution of inorganic salts is added to the solution to provide the organic solvent with sufficient electric conductivity for electrical particle measurement. Such substances include one of the following.

Compound (a): a zwitterionic compound or compounds, or

Compound (b): a compound or compounds including a hydroxyl group and a carboxyl or an amino group in the same molecule The invention further provides an electrolyte solution for a particle measuring apparatus that can be used as a dispersion medium or sheath solution for both optical and electrical particle measurement.

While not wishing to be limited thereto in any way, the principle by which the inventor believes the present invention solves the problems mentioned earlier will now be explained. For a solution to have electric conductivity, an ionic substance must be present in the solvent in an ionized state. This may be accomplished by dissolving a salt in the solvent. When water is used as the solvent, the salt dissolves and ionizes in the following manner. The negative polar portions (oxygen atom portions) of the water molecules bond to the cations of the salt. The positive polar portions (hydrogen atom portions) of the water molecules bond to the anions of the salt. The cations and anions are surrounded by water molecules undergoing an electrostatic synergistic effect. The fact that each ion is surrounded by water molecules means that a distance is created between the bonded ions, resulting in an ionized state. Thus, ionization readily occurs in water, so that an electrolyte solution is easily obtained.

Ionization in an organic solvent is generally considered to be difficult when an inorganic salt is used as the ionic substance. This is thought to be because, for inorganic salts, the solvent molecules, unlike water molecules, do not facilitate dissociation of the bonded ions.

The present invention achieves desired conductivity of organic solvents by adding to an organic solvent a substance that causes dissociation of the bonded ions, i.e., a substance that promotes dissolution of inorganic salts (hereafter "auxiliary substances"), thereby promoting ionization of the ionic substance in the organic solvent. The aforementioned compounds (a) and (b) are both auxiliary substances.

A zwitterionic compound has both a cationic portion and an anionic portion in the same molecule. The cation of the inorganic salt is surrounded by the anionic portion of the zwitterionic compound molecule, while the anion is surrounded by the cationic portion of the zwitterionic compound molecule. Thus, each ion is surrounded by zwitterionic compound molecules, so that a distance is created between the cations and anions.

The auxiliary substance used may also be a compound which includes a hydroxyl group and a carboxyl or an amino group in the same molecule. When a compound with a hydroxyl group and a carboxyl group in the same molecule is used, the anion portions of the hydroxyl group and carboxyl group of the compound molecule surround the cations, with the result that the cations become surrounded by the compound molecules. This creates a distance between the cations and anions.

When a compound with a hydroxyl group and an amino group in the same molecule is used, the cation portions of the hydroxyl group and carboxyl group of the compound molecule surround the anions, with the result that the anions become surrounded by the compound molecules. This creates a distance between the cations and anions.

Thus, the present invention allows dissolution and ionization of inorganic salts in organic solvents, thereby providing electrolyte solutions with electrolyte conductivity sufficient for electrical particle measurement.

DESCRIPTION OF THE PREFERRED EMBODIMENTS

Figure 1:
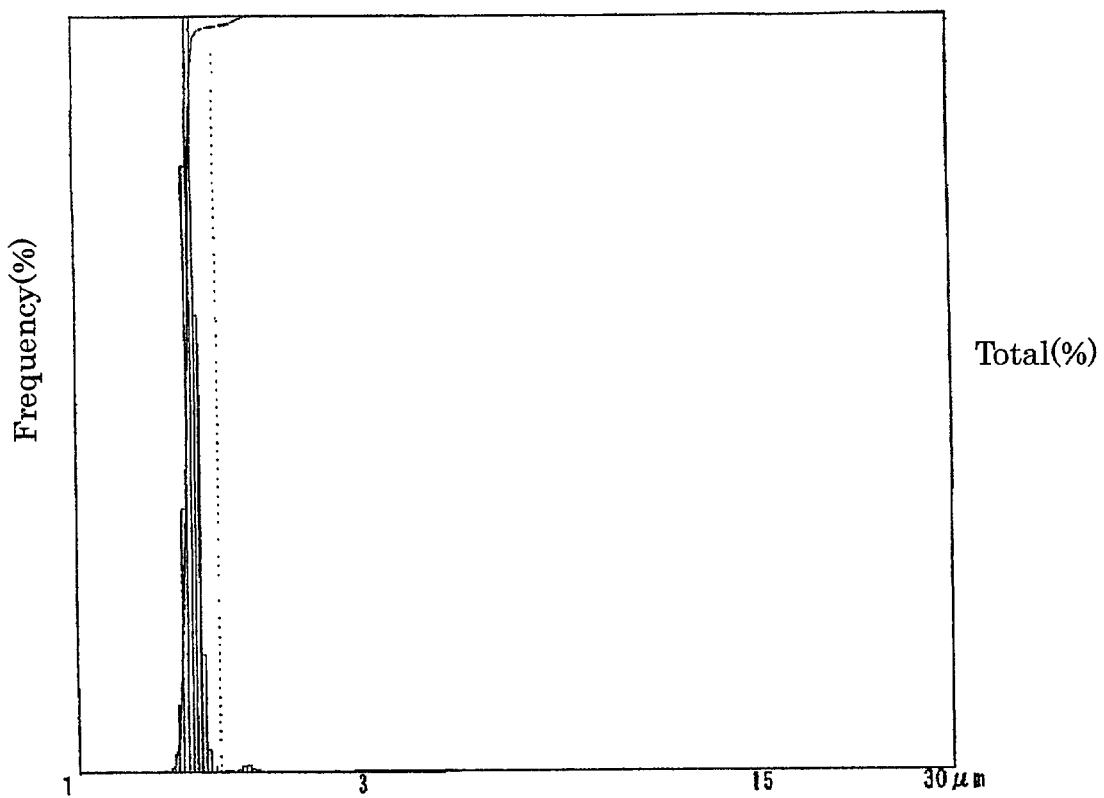
FIG. 1 shows a particle size distribution obtained by measurement of latex particles using an electrolyte solution for a particle measuring apparatus according to the invention and an SD-2000 electrical particle measuring apparatus (product of Sysmex Co., Ltd.).

The present invention will be explained in detail with reference to the drawings. The present invention is not limited to the following explanation.

As organic solvents for the invention there may be used organic compounds such as methanol, ethanol, isopropanol, acetone and similar compounds. Any one or combination of two or more of these may be used upon selection based on the properties of the particles to be measured and the type of inorganic salt to be used. For example, for measurement of particles of such a nature that they readily aggregate when methanol alone is used as the organic solvent, a mixture of methanol and isopropanol may be used.

The effect of the auxiliary substance allows a variety of inorganic salts to be used for the invention. Sodium chloride and calcium chloride are preferred for use. Any one or combination of two or more of these may be used upon selection based on the relationship between the properties of the particles to be measured and the type of organic solvent.

A zwitterionic compound may be used as the auxiliary substance of the invention. A compound with a hydroxyl group and a carboxyl or amino group in the same molecule may also be used as the auxiliary substance of the invention.

Amino acids, amphoteric surfactants and similar compounds may be used as zwitterionic compounds. As amino acids there may be used, for example, α-amino acids such as serine and threonine and β-amino acids such as β-alanine, or oligopeptides with a plurality of amino acids connected by peptide bonds. Betaine may be used as an amphoteric surfactant.

Among compounds with a hydroxyl group and a carboxyl or amino group in the same molecule, compounds with a hydroxyl group and a carboxyl group in the same molecule include malic acid, citric acid, lactic acid and similar compounds. Compounds with a hydroxyl group and an amino group in the same molecule include 2-aminoethanol, 3-aminopropanol and similar compounds.

Although compounds with a hydroxyl group, a carboxyl group and an amino group in the same molecule may be used as auxiliary substances, such substances are included among the aforementioned zwitterionic compounds for the purpose of the present specification. Serine and threonine qualify as such compounds.

Numerous compounds may therefore be used as auxiliary substances, but they will often be used in combinations of two or more types instead of only one type. For example, there may be used the combinations of betaine and malic acid, betaine and citric acid, betaine and lactic acid, betaine and 2-aminoethanol, 2-aminoethanol and malic acid, 2-aminoethanol and citric acid or 2-aminoethanol and lactic acid.

The combinations of compounds that may be used as organic solvents, inorganic salts and auxiliary substances are numerous, but preferred for use are the combination of methanol, sodium chloride and betaine, the combination of methanol, sodium chloride and malic acid, the combination of methanol, sodium chloride and citric acid, the combination of methanol, sodium chloride and lactic acid, and the combination of methanol, sodium chloride and 2-aminoethanol.

The amount of the inorganic salt dissolved in the organic solvent must be such as to produce electric conductivity sufficient for electrical particle measurement. The electric conductivity may be, for example, 10 mS/cm or greater. The appropriate amount of the auxiliary substance is calculated based on the amount of the inorganic salt in the organic solvent. The electrolyte solution of the invention which is prepared with the above-mentioned organic solvent, inorganic salt and auxiliary substance is preferably adjusted to have a viscosity suitable to permit operation of the fluid system mechanism of the particle measuring apparatus used.

Experimental Examples

Experimental examples of the invention will now be described.

EXAMPLE 1

(Electrolyte Solution Preparation 1)

For this operation, methanol was used as the organic solvent, sodium chloride was used as the inorganic salt and malic acid, lactic acid, 2-aminoethanol and betaine were used as auxiliary substances.

Table 1 shows equimolar amounts of each of the auxiliary substances with respect to 1.00 g of sodium chloride.

TABLE 1

| auxiliary substances | |
| --- | --- |
| malic acid | 2.29 g |
| lactic acid | 1.48 mL |
| 2-aminoethanol | 1.03 mL |
| betaine | 2.00 g |

First, each of the substances was prepared based on Table 1, each was dissolved in 100 mL of methanol, and the electric conductivity was measured.

Sodium chloride was added to each of the prepared solutions at equimolar and ½ molar amounts with respect to the auxiliary substances (1.00 g and 0.50 g of sodium chloride), and the electric conductivity was measured.

Table 2 shows the results of these measurements.

TABLE 2

| auxiliary substances | | sodium chloride | electric conductivity (mS/cm) |
| --- | --- | --- | --- |
| malic acid | 2.29 g | 0.00 g | 0.220 |
| | 2.29 g | 0.50 g | 4.74 |
| | 2.29 g | 1.00 g | 8.43 |
| lactic acid | 1.48 mL | 0.00 g | 0.0468 |
| | 1.48 mL | 0.50 g | 4.75 |
| | 1.48 mL | 1.00 g | 8.44 |
| 2-aminoethanol | 1.03 mL | 0.00 g | 0.120 |
| | 1.03 mL | 0.50 g | 4.86 |
| | 1.03 mL | 1.00 g | 8.55 |
| betaine | 2.00 g | 0.00 g | 0.0190 |
| | 2.00 g | 0.50 g | 4.92 |
| | 2.00 g | 1.00 g | 8.25 |

Virtually no electric conductivity was measured for the solutions containing only the auxiliary substances dissolved in methanol, but upon addition of sodium chloride the electric conductivity increased almost in direct proportion to the amount. These results suggest that sodium chloride was more easily ionized in methanol by the effect of the auxiliary substances.

EXAMPLE 2

(Electrolyte Solution Preparation 2)

For this operation, of the combination of substances used in electrolyte solution preparation 1 there were selected methanol as the organic solvent, sodium chloride as the inorganic salt and betaine as the auxiliary substance.

First, 1.20 g of sodium chloride was dissolved in 100 mL of a betaine/methanol solution containing 4.00 g of dissolved betaine. Sodium chloride was then further added 0.10 g at a time to determine the saturation amount of sodium chloride in 100 mL of the betaine/methanol solution (containing 4.00 g of betaine). The electric conductivity of the solution was measured at each state of sodium chloride addition. The results are shown on Table 3.

TABLE 3

| betaine (g) | sodium chloride (g) | Dissolved completely? | electric conductivity (mS/cm) |
|---|---|---|---|
| 4.00 | 1.20 | Yes | 9.14 |
| 4.00 | 1.30 | Yes | 9.64 |
| 4.00 | 1.40 | Yes | 10.19 |
| 4.00 | 1.50 | No | 10.55 |
| 0.00 | 1.00 | No | 3.30 |

Table 3 indicates that the saturation amount of sodium chloride in the solution was higher than at least 1.40 g. On the other hand, when 1.00 g of sodium chloride was added to 100 mL of methanol (without betaine), it did not completely dissolve. This result demonstrates that betaine has an effect of increasing the solubility of salts.

As seen by the data for the stage of 1.40 g addition of sodium chloride and the stage of 1.50 g (i.e., saturation of sodium chloride) in Table 3, the electric conductivity improved to 10.19 mS/cm and 10.55 mS/cm, respectively. These electric conductivity values were sufficient for electrical particle measurement.

EXAMPLE 3

(Electrical Particle Measurement)

The following explanation concerns an experiment in which an electrolyte solution of the invention was used for measurement of the particle size distribution and mean particle size of latex particles. (This measurement will be termed "particle measurement A"). For particle measurement A, based on the electrolyte solution prepared for electrolyte solution preparation 2 there was selected a methanol solution containing 1.40 g of sodium chloride and 4.00 g of betaine in 100 mL (electric conductivity: 10.19 mS/cm), and this methanol solution was used as the sheath solution and dispersion medium. The sample solution was prepared by dispersing latex particles (particle size: 1.588 μm, Particle-Size Standards by Duke Scientific Corporation) in the dispersion medium.

For contrast with particle measurement A, a conventional electrolyte solution employing water as the solvent (CELLSHEATH, product of Sysmex Co., Ltd.) was used as the sheath solution and dispersion medium, and the same latex particles as above were dispersed in this dispersion medium to prepare a sample solution for measurement of the particle size distribution and mean particle size. (This measurement will be termed "particle measurement B").

An SD-2000 by Sysmex Co., Ltd. was used as the particle measurement apparatus for particle measurements A and B. This apparatus is an electrical particle measuring apparatus employing a sheath flow system. For measurement of particles with this apparatus, it is necessary for the sample solution in which the particles to be measured are dispersed and the sheath solution to both be electrolyte solutions, and each of the sample solutions and sheath solutions used for particle measurement A and B are electrolyte solutions, as explained above.

The electrical signals that are detected will include false signals or electrical noise signals which are clearly of different sizes than those for the particles to be measured, and these can adversely affect the measurement results. These signals must be excluded from the standpoint of achieving more accurate measurement results. Preferably, a threshold is set for the detection results to establish a fixed range in which the probability of particles to be measured is thought to be high, and analysis of the mean particle size, etc. carried out within this range. For particle measurement A and B, the threshold for the particle size was 1.36 μm as the lower limit and 1.73 μm as the upper limit, and the analysis was carried out within this range.

FIG. 1 is a particle size distribution graph obtained as the result of particle measurement A. The horizontal axis is the particle size expressed as a logarithmic transformation, and the frequency of particles of each particle size is indicated based on the number of particles. The major analysis results for particle measurement A were as follows.

Mean particle size=1.56 μm
Particle size SD=0.03 μm
Particle size CV=2.15%
(Particle concentration=1562/μL, count=46,849)

Figure 2:
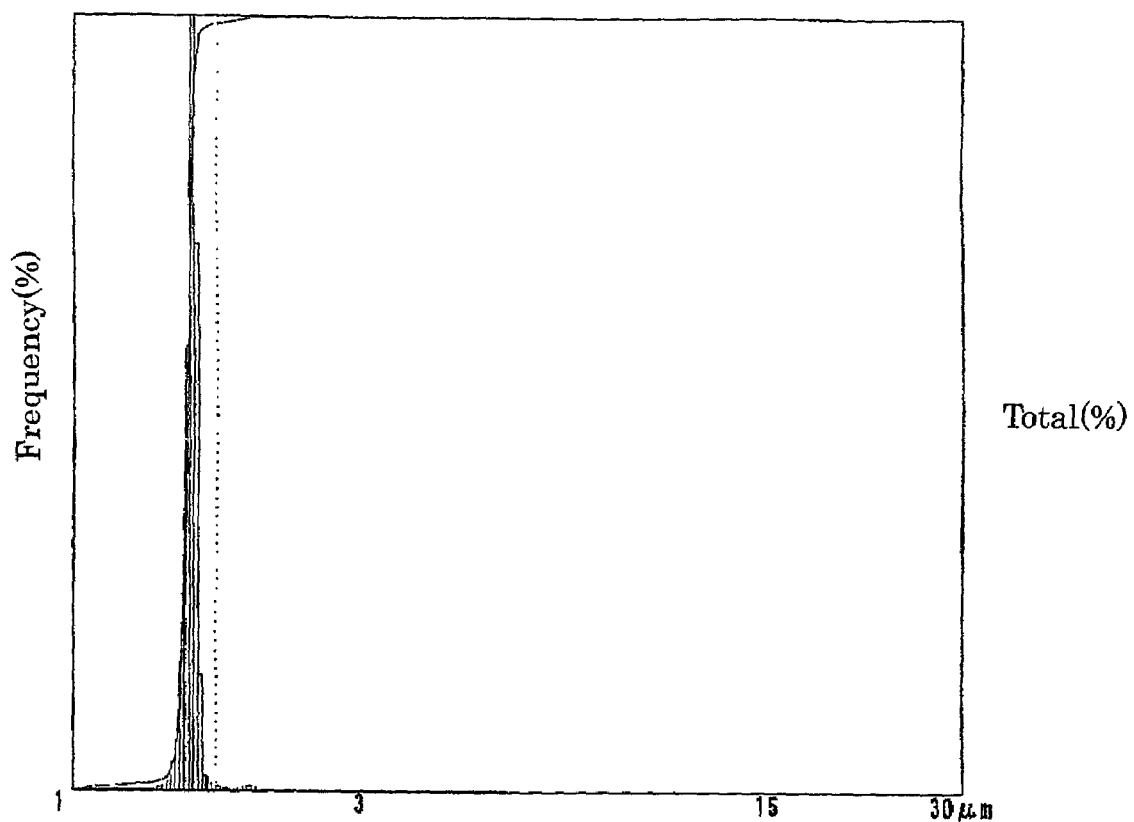
FIG. 2 shows a particle size distribution obtained by measurement of latex particles using a conventional electrolyte solution employing water as the solvent (CELLSHEATH, product of Sysmex Co., Ltd.) and an SD-2000 electrical particle measuring apparatus (product of Sysmex Co., Ltd.).

FIG. 2 is a particle size distribution graph obtained as the result of particle measurement B. The horizontal axis is the particle size expressed as a logarithmic transformation, and the frequency of particles of each particle size is indicated based on the number of particles. The major analysis results for particle measurement B were as follows.

Mean particle size=1.56 μm
Particle size SD=0.03 μm
Particle size CV=2.15%
(Particle concentration=1492 μL, count=44,762)

For both particle measurement A and B, the respective particle size distributions for particle measurement A and B in FIGS. 1 and 2 were identical under approximately the same conditions with a particle concentration of about 1500/μL and a count of about 45,000. This indicates that the electrolyte solution of the invention used for particle measurement A functions in the same manner as a conventional electrolyte solution using water as the solvent.

EXAMPLE 4

(Comparison Between Electrical Particle Measurement and Optical Particle Measurement)

The following explanation concerns "particle measurement C" and "particle measurement D" as an experiment measuring commercially available cocoa powder (water-soluble particles) using an electrolyte solution according to the invention. The particle measuring apparatus used for particle measurement C was an SD-2000 by Sysmex Co., Ltd., as for particle measurements A and B. As mentioned above, this is an electrical particle measuring apparatus. An FPIA-2100 optical particle measuring apparatus by Sysmex Co., Ltd. was used for particle measurement D. This is an optical particle measuring apparatus, and more specifically, it utilizes a method in which a sample solution containing the particles and a sheath solution are allowed to flow through a flat flow cell to form a sheath flow, and the particle images are taken with a CCD camera by irradiation with a strobe lamp. The obtained image is then analyzed to count the particles and measure their sizes. The same sample solution and sheath solution were used for both particle measurements C and D. That is, particle measuring apparatuses based on different principles were used for particle measurements C and D, while the other conditions were the same.

The sheath solution used was a solution prepared with the same composition as the solution with the highest electric conductivity among the solutions in which the sodium chloride dissolved completely according to the results of electrolyte solution preparation 2 above, or in other words, the solution with 4.00 g of betaine and 1.40 g of sodium chloride dissolved with respect to 100 mL of methanol.

The sample solution was prepared in the following manner. First, 0.5 g of cocoa powder was added to and dispersed in 50 mL of isopropanol. (This will hereunder be referred to as the "dispersion sample".) Next, 0.2 mL of the dispersion sample was added to 50 mL of the sheath solution prepared in the manner described above to prepare the sample solution. Here, two types of organic solvents, methanol and isopropanol, were used for preparation of the electrode solution, for the purpose of reducing aggregation of the cocoa powder as the particles to be measured for particle measurement C and D.

For particle measurement C, the threshold for the particle size was 2.00 µm as the lower limit and 60.0 µm as the upper limit, and the analysis was carried out within this range. For particle measurement D the threshold could not be set exactly the same since the particle measuring apparatus was a different type than for particle measurement C, but as a result of approximating that setting as closely as possible, the threshold for the particle size was 2.00 µm as the lower limit and 61.6 µm as the upper limit, and the analysis was carried out within this range. Although the upper limits are slightly different, this is not considered a problem for comparison of the measurement results for C and D.

Figure 3:
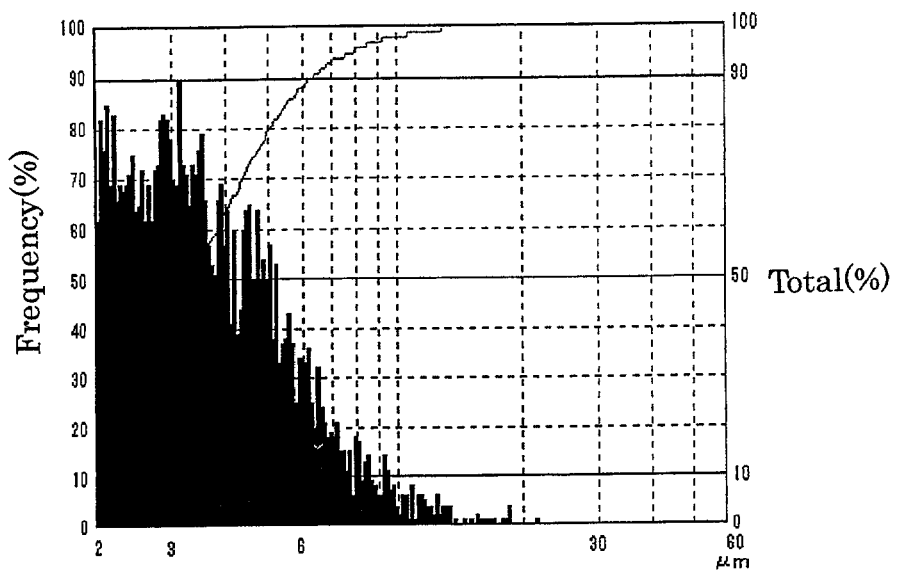
FIG. 3 shows a particle size distribution obtained by measurement of cocoa powder using an electrolyte solution for a particle measuring apparatus according to the invention and an SD-2000 electrical particle measuring apparatus (product of Sysmex Co., Ltd.).

FIG. 3 is a particle size distribution graph obtained as a result of particle measurement C. The horizontal axis is the particle size expressed as a logarithmic transformation, and the frequency of particles of each particle size is indicated based on the number of particles. The major analysis results were as follows.

Mean particle size=4.01 µm
Particle size SD=2.03 µm
Particle size CV=50.6%

Figure 4:
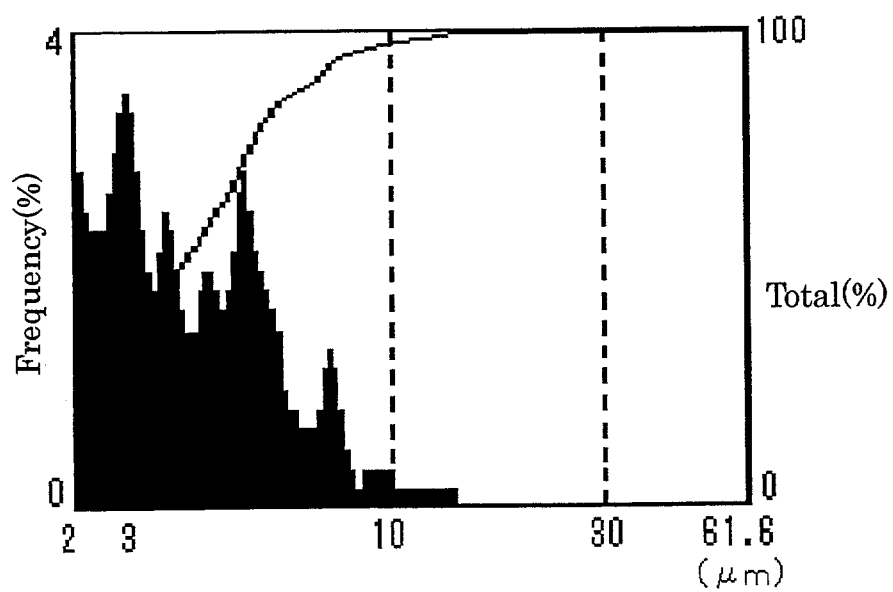
FIG. 4 shows a particle size distribution obtained by measurement of cocoa powder using an electrolyte solution for a particle measuring apparatus according to the invention and an FPIA-2100 optical particle measuring apparatus (product of Sysmex Co., Ltd.).

FIG. 4 is a particle size distribution graph obtained as the result of particle measurement D. The horizontal axis is the particle size expressed as a logarithmic transformation, and the frequency of particles of each particle size is indicated based on the number of particles. The major analysis results were as follows.

Mean particle size=4.12 µm
Particle size SD=2.05 µm
Particle size CV=49.74%

The particle size distribution graphs for particle measurements C and D both exhibited maximum peaks at around a particle size of 3 µm, and thereafter with increasing particle size, the particle distribution decreased overall with repetition of some peaks. Thus, the particle size distribution graphs for particle measurements C and D showed similar tendencies. Upon comparing the results of analysis of particle measurements C and D, they were found to be almost the same for each parameter, and considering that the two measurement results were obtained using separate particle measuring apparatuses based on different measuring principles, the numerical differences in the analysis results may be considered within the acceptable range of error.

In other words, the results for particle measurements C and D indicate that an electrolyte solution of the invention used for particle measurement with an electrical particle measuring apparatus can also be used for particle measurement with an optical particle measuring apparatus. The electrolyte solution of the invention could be satisfactorily used for optical particle measurement because of its colorless and transparent composition.

Thus, by employing a substance that promotes ionization of inorganic salts in organic solvents, the present invention has realized an electrolyte solution with electric conductivity sufficient for electrical particle measurement. It is thereby possible to provide an electrolyte solution for an electrical particle measuring apparatus that employs an organic solvent as the solvent and does not accelerate corrosion of particle analysis devices.

The invention also provides an electrolyte solution that can be used as a sheath solution or dispersion medium for both electrical particle measuring apparatuses and optical particle measuring apparatuses.

As was clearly demonstrated by the examples, the electrolyte solution for a particle measuring apparatus according to the invention may be used as a sheath solution or dispersion medium for a particle measuring apparatus employing a sheath flow system, but it may also be used as a dispersion medium for a particle measuring apparatus that does not employ a sheath flow system.

The invention has been described with reference to certain preferred embodiments but it will be appreciated that variations and modifications can be effected within the spirit and scope of the invention.

What is claimed is:

1. A nonaqueous electrolyte solution for a particle measuring apparatus comprising:
   an organic solvent;
   an inorganic salt; and
   a zwitterionic compound.

2. An electrolyte solution for a particle measuring apparatus according to claim 1, wherein said organic solvent comprises methanol, ethanol, isopropanol or acetone, or a combination of two or more thereof.

3. An electrolyte solution for a particle measuring apparatus according to claim 1, wherein said inorganic salt comprises sodium chloride, calcium chloride or a combination thereof.

4. An electrolyte solution for a particle measuring apparatus according to claim 1, wherein said zwitterionic compound is an amino acid.

5. An electrolyte solution for a particle measuring apparatus according to claim 1, wherein said zwitterionic compound is an amphoteric surfactant.

6. An electrolyte solution for a particle measuring apparatus according to claim 4, wherein said amino acid is serine, threonine, β-alanine or a combination of two or more thereof.

7. An electrolyte solution for a particle measuring apparatus according to claim 5, wherein said amphoteric surfactant is betaine.

8. A nonaqueous electrolyte solution for a particle measuring apparatus comprising:
   an organic solvent;
   an inorganic salt selected from the group consisting of sodium chloride, calcium chloride and a combination thereof; and
   a substance that promotes dissolution of inorganic salts, which is betaine.

9. A nonaqueous electrolyte solution for a particle measuring apparatus comprising:
   an organic solvent which is a mixture of methanol and isopropanol;
   an inorganic salt which is sodium chloride; and
   a substance that promotes dissolution of inorganic salts which is betaine.

10. A nonaqueous electrolyte solution for a particle measuring apparatus, which comprises methanol, sodium chloride and betaine.

* * * * *